United States Patent [19]

Schmidt et al.

[11] 4,080,307

[45] Mar. 21, 1978

[54] NEW ADDITIVES FOR LUBRICANTS

[75] Inventors: Andreas Schmidt, Reinach, Switzerland; Peter Collen Hamblin, Wilmslow, England

[73] Assignee: Ciba-Geigy AG, Basel, Switzerland

[21] Appl. No.: 785,273

[22] Filed: Apr. 6, 1977

[30] Foreign Application Priority Data

Apr. 12, 1976 Switzerland .................... 4614/76

[51] Int. Cl.$^2$ .................... C10M 1/48; C10M 3/42; C10M 5/24; C10M 7/46
[52] U.S. Cl. .................... 252/32.7 E; 252/32.5; 260/501.12
[58] Field of Search .................... 252/32.5, 32.7 E; 260/501.12

[56] References Cited

U.S. PATENT DOCUMENTS

| | | | |
|---|---|---|---|
| 3,488,408 | 1/1970 | Birum et al. | 252/32.5 |
| 3,682,819 | 8/1972 | Morris et al. | 252/32.7 E |
| 3,725,466 | 4/1973 | Uhing | 252/48.2 |

OTHER PUBLICATIONS

Bulletin of the Academy of Science USSR, 1969, p. 436, Hydrolysis of Bis(chloromethyl)thiophosphonic Acid by Ivasyuk et al.
1,3-Thiaphosphetane Derivatives by Gilyazov et al. in Izvestiza Akademii Nauk SSSR, Seriya Khimicheskaya, No. 5, May 1970, pp. 1177–1180.

*Primary Examiner*—Delbert E. Gantz
*Assistant Examiner*—Irving Vaughn
*Attorney, Agent, or Firm*—Luther A. R. Hall

[57] ABSTRACT

New ammonium salts of 1,3-oxa- or 1,3-thia-phosphetanes are suitable additives for mineral and/or synthetic lubricants.

15 Claims, No Drawings

NEW ADDITIVES FOR LUBRICANTS

The present invention relates to new ammonium salts of oxa- and thia-phosphetanes and their use as additives for lubricants and to the lubricating oil formulations provided with the new compounds.

In general, various additives are added to mineral and synthetic lubricants in order to improve their properties in use. In particular, there is a need for additives which should protect the devices to be lubricated from wear due to friction. The demand made on wear inhibitors of this type is that they increase the load-bearing capacity of the lubricant and do not have a corrosive action on the metal parts to be protected. It is known from British patent specification No. 1,268,561 to use ammonium salts of cyclic alkyldithiophosphoric acids as additives for lubricating oils.

A new category of ammonium salts of oxa- and thia-phosphetanes, the activity of which greatly exceeds that of known high-pressure additives for lubricants has, surprisingly, now been found.

The new compounds correspond to the general formula I

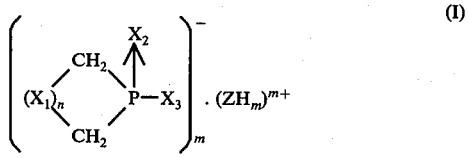

in which $X_1$, $X_2$ and $X_3$ independently of one another denote O or S and, if $X_1$ is O, $n$ denotes 1 and, if $X_1$ is S, $n$ denotes 1-6, and Z is a mono-acidic or di-acidic, nitrogen-containing, oil-soluble organic base and, if Z is a mono-acidic base, $m$ denotes 1 and, if Z is a di-acidic base, $m$ denotes 2.

The formula I comprises the following basic types of ammonium salts of 1,3-oxa- or 1,3-thia-phosphetanes:

Ammonium salts of 1,3-oxaphosphetanes of the formula I are those in which $X_1$, $X_2$ and $X_3$ are O; those in which $X_1$ is O, one of $X_2$ and $X_3$ is O and the other is S; and those in which $X_1$ is O and $X_2$ and $X_3$ are S, $n$ always being 1 in the oxa compounds.

Ammonium salts of 1,3-thiaphosphetanes of the formula I are those in which $X_1$, $X_2$ and $X_3$ are S; those in which $X_1$ is S, one of $X_2$ and $X_3$ is S and the other is O; and those in which $X_1$ is S and $X_2$ and $X_3$ are O, $n$ having a value of 1 to 6, and especially of 1, in the thia compounds.

Preferred ammonium salts of phosphetanes of the formula I are those in which $X_1$ is S and $X_2$ and $X_3$ are O and $n$ is 1 to 6 and preferably 1.

In principle, any mono-acidic or di-acidic organic nitrogen base can be used as the base for forming a salt with the 1,3-oxa- or 1,3-thia-phosphetanes. For practical reasons, however, only oil-soluble nitrogen bases and especially those with a total C number of 6-40 C atoms are suitable for use in lubricants. Thus, for example, the phosphetanes which are not in the form of a salt and are described in British patent specification No. 1,212,931, and also their salts with ammonia, are unsuitable as additives for lubricants.

Monovalent compounds, and especially primary, secondary or tertiary amines of the formula $(R_1)R_2NR_3$, in which $R_1$ and $R_2$ independently of one another denote hydrogen or an aliphatic or aromatic radical and $R_3$ denotes an aliphatic or aromatic radical, are preferably employed as the oil-soluble organic nitrogen bases.

If $R_1$, $R_2$ and $R_3$ denote an aliphatic radical, this radical can be branched or straight-chain alkyl, which is optionally interrupted by -O- and/or -S-, such as methyl, ethyl, n-propyl, isopropyl, t-butyl, amyl, hexyl, 1-methylpentyl, t-octyl, 2-ethyl-hexyl, n-decyl, n-dodecyl, 2-ethyl-decyl, n-tetradecyl, n-octadecyl, n-eicosyl, 2,7,8-trimethyl-decyl, 4-isobutyl-2,5-dimethyl-heptyl, octacosoyl, dotriacontyl, hexatriacontyl or tetracontyl. $R_1$, $R_2$ and $R_3$ can, however, as an aliphatic radical, also be branched or straight-chain alkenyl, which is optionally interrupted by -O- or -S-, such as allyl, vinyl, 2-butenyl, 2-hexenyl, 2-dodecenyl or 2-hexatriacontenyl. The total C number of the radicals $R_1$, $R_2$ and $R_3$ should be 6 to 40.

The amino group can optionally also be ethoxylated and in this case the degree of ethoxylation must be brought into accord with the solubility in oil which is sought for the product.

If $R_1$, $R_2$ and $R_3$ denote an aromatic radical, this radical is a phenyl group which is optionally substituted by alkyl groups, each with 1 to 12 C atoms, such as methyl, ethyl, propyl, butyl, hexyl, octyl, decyl or dodecyl.

Amongst the organic nitrogen bases of the formula $(R_1)R_2NR_3$, which are to be used, those to be mentioned are those in which $R_1$ and $R_2$ independently of one another denote hydrogen or an aliphatic radical and $R_3$ denotes a phenyl group which is optionally substituted by alkyl groups.

However, primary organic nitrogen bases of the formula $H_2NR_3$, in which $R_3$ denotes branched or straight-chain alkyl or alkenyl, each with 6 to 40, and especially each with 8 to 24, C atoms, which are optionally interrupted by —O— or —S—, are particularly preferentially employed.

In practice, mixtures of different nitrogen bases, such as, for example, Primene 81-R (mixture of primary $C_{12}$–$C_{15}$ t-alkylamines, from Rohm and Haas, U.S.A.), are frequently employed. However, the salts which possess a single nitrogen component are also equally suitable.

Examples of such amines are: methylamine, ethylamine, propylamine, butylamine, t-butylamine, hexylamine, octylamine, (2-ethylhexyl)-amine, t-octylamine, decylamine, t-dodecylamine, tetradecylamine, octadecylamine, phenylamine, benzylamine, (nonylphenyl)-amine, cyclohexylamine, pyridine, piperidine, dimethylamine, methyloctylamine, didodecylamine, methyloctadecylamine, methylcyclohexylamine, phenyloctylamine, trimethylamine, dimethylcyclohexylamine, methyloctyldecylamine, (octoxyethyl)-amine, (octylthioethyl)-amine, (t-dodecylthioethyl)-amine, dodecyl-dimethylamine, hexadecyl-dimethylamine, octadecyl-dimethylamine, tridecyl-dimethylamine, decyldimethylamine, didodecylmethylamine, methyl-butyl-dodecylamine, dimethyl-propylamine, trioctyl-amine, dioctyl-methylamine, dodecylbenzyl-methylamine, nonylphenyl-dimethylamine, phenyldodecyl-methylamine, phenyl-dimethylamine, phenyl-dimethylamine, allyl-dibutylamine, methyl-dodecenylamine, heptadecyl-dimethylamine, dioctyl-methylamine, methyl-α-naphthyl-phenylamine, cyclohexyl-dimethylamine, nonyl-dimethylamine, tris-(n-tridecyl)-amine, tris-(n-dodecyl)-amine, tris-(isooctyl)-amine, methylbutylhexadecylamine, triethylamine, 3,5-dimethylpyridine, 2-(ethylhexyl)-methyl-dodecylamine, (methylethyl)-didecylamine, methyl-butyl-dodecylamine, dimethyl-dodecylamine, hexadecyl-dimethylamine, tris-(i-dodecyl)-amine, dimethyl-benzylamine, dimethyl-(tert.-octylphenyl)-amine, (N-methyl)-1-imidazoline (N-methyl)-1-pyrrazoline, oxazoline, quinoline, pyrrolidine, N-ethylpyrrolidine, N-methyl-piperidine, N-butyl-piperidine, thiazole and N-methyl-phenothiazine.

Compounds of the formula I in which $X_1$ is S and $n$ is 1–6 and $X_2$ and $X_3$ denote O and Z is a primary, secondary or tertiary amine of the formula $(R_1)R_2NR_3$, in which $R_1$ and $R_2$ independently of one another denote hydrogen or an aliphatic or aromatic radical and $R_3$ denotes an aliphatic or aromatic radical, are preferred.

Compounds of the formula I in which $X_1$ is S and $n$ is 1–6 and $X_2$ and $X_3$ denote O and Z is a primary amine of the formula $H_2NR_3$, in which $R_3$ denotes an aliphatic radical, and $m$ is 1, are particularly preferred.

Examples of compounds of the formula I are: dodecylammonium salt of 3-hydroxy-3-oxo-1,3-thiaphosphetane, di-n-butyl-ammonium salt of 3-mercapto-3-thio-1,3-thiaphosphetane, tri-n-octyl-ammonium salt of 3-hydroxy-3-oxo-1,3-thiaphosphetane, (2,6-di-t.-butylphenyl)-ammonium salt of 3-mercapto-3-oxo-1,3-oxaphosphetane, (2,6-diethyl-phenyl)-diethylammonium salt of 3-hydroxy-3-oxo-1,3-thiaphosphetane, tri-n-nonyl-ammonium salt of 3-hydroxy-3-oxo-1,3-oxaphosphetane and di-(2-ethyl-hexyl)-ammonium salt of 3-hydroxy-3-oxo-1,3-thiaphosphetane.

The new compounds of the formula I are manufactured according to processes which are in themselves known. Approximately $m$ mols of a phosphetane of the formula

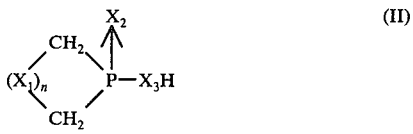

are reacted with approximately one mol of an organic nitrogen base. The reaction can optionally also be carried out with a slight excess of acid. The reaction can be carried out in an inert organic solvent, such as, for example, toluene, benzene or xylene, or in a mineral oil but it can also be carried out without a solvent, in which case the desired compounds are obtained direct in adequate purity. The reaction temperature is not critical for the reaction and the process can be carried out at room temperature and, if it is carried out in a solvent, can even proceed at the reflux temperature. The reaction itself proceeds exothermically. Preferably, the reaction is carried out at room temperature and without external cooling.

The manufacture of compounds of the formula II is known and is described, for example, in Bull.Acad.-Sci.USSR, 1969, 436; in Izv. Akad. Nauk SSSR, Ser. Khim. 1969 (2), 481–482, in Izv. Akad.Nauk SSSR, Ser. Khim. 1970 (5), 1177–1180 or in French Pat. No. 1,558,199.

Even in very small amounts, the compounds of the formula I act as high-pressure additives in lubricants. Thus, mineral and synthetic lubricating oils, and also mixtures thereof, which are provided with 0.001 to 5% by weight, and preferably 0.02 to 3%, relative to the lubricant, of a compound of the formula I display excellent high-pressure lubricating properties which manifest themselves in greatly reduced wear phenomena of the parts which rub against one another and are to be lubricated. The lubricants which can be used are commonly known to those skilled in the art and are described, for example, in "Schmiermittel Taschenbuch" ("Lubricants Handbook") (Huthig Verlag, Heidelberg, 1974).

The lubricating oil formulation can additionally also contain other additives which are added in order to improve certain basic oil properties, such as antioxidants, metal passivators, rust inhibitors, agents which improve the viscosity index, pour-point depressors, dispersants/detergents and other additives which protect against wear.

Examples of antioxidants are:

(a) alkylated and non-alkylated aromatic amines and mixtures thereof, for example: dioctyldiphenylamine, mono-t-octylphenyl-$\alpha$- and -$\beta$-naphthylamines, phenothiazine, dioctylphenothiazine, phenyl-$\alpha$-naphthylamine and N,N'-di-sec-butyl-p-phenylenediamine, (b) sterically hindered phenols, for example 2,6-di-tert-butyl-p-cresol, 4,4'-bis-(2,6-diisopropylphenol), 2,4,6-triisopropylphenol, 2,2'-thio-bis-(4-methyl-6-tertphenol) and 4,4'-methylene-bis-(2,6-di-tert-butylphenol), (c) alkyl phosphites, aryl phosphites or alkaryl phosphites, for example: trinonyl phosphite, triphenyl phosphite and diphenyldecyl phosphite, (d) esters of thiodipropionic acid or thiodiacetic acid, for example: dilauryl thiodipropionate or dioctyl thiodiacetate, (e) salts of carbamic and dithiophosphoric acids, for example: antimony diamyldithiocarbamate and zinc diamyldithiophosphate, and (f) combinations of two or more antioxidants from the above, for example: an alkylated amine and a sterically hindered phenol.

Examples of metal passivators are:

(a) for copper, for example, benztriazole, tetrahydrobenztriazole, 2-mercaptobenzthiazole, 2,5-dimercaptothiadiazole, salicylidene-propylenediamine and salts of salicylaminoguanidine, (b) for lead, for example, sebacic acid derivatives, quinizarine and propyl gallate, and (c) a combination of two or more of the above additives.

Examples of rust inhibitors are:

(a) organic acids and their esters, metal salts and anhydrides, for example: N-oleoyl-sarcosine, sorbitane monooleate, lead naphthenate and dodecenylsuccinic anhydride, (b) nitrogen-containing compounds, for example:

I. primary, secondary or tertiary aliphatic or cycloaliphatic amines and amine salts of organic and inorganic acids, for example oil-soluble alkyl-ammonium carboxylates, and II. heterocyclic compounds, for example: substituted imidazolines and oxazolines, (c) phosphorus-containing compounds, for example: amine salts of phosphoric acid partial esters, (d) sulphur-containing compounds, for example: barium dinonylnaphthalene-sulphonates and calcium petroleum sulphonates, and (e) combinations of two or more of the above additives.

Examples of agents which improve the viscosity index are, for example: polymethacrylates, vinylpyrrolidone/methacrylate copolymers, polybutenes, olefine copolymers and styrene/acrylate copolymers.

Examples of pour-point depressors are, for example: polymethacrylates and alkylated naphthalene derivatives.

Examples of dispersants/detergents are, for example: polybutenylsuccinic acid imides, polybutenylphosphonic acid derivatives and hyperbasic sulphonates and phenolates of magnesium, calcium and barium.

Examples of other additives which provide protection against wear are, for example, compounds which contain sulphur and/or phosphorus and/or halogen, such as vegetable oils treated with sulphur, zinc dialkyldithiophosphates, tritolyl phosphate, chlorinated paraffins, alkyl disulphides and aryl disulphides.

The examples which follow illustrate the invention.

EXAMPLE 1

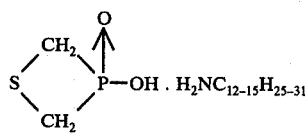

26.7 g (0.215 mol) of 3-hydroxy-3-oxo-1,3-thiaphosphetane are suspended in 200 ml of toluene and 37.5 g (0.196 mol) of Primene 81-R (mixture of primary $C_{12}$–$C_{15}$ t-alkylamines, Rohm and Haas, U.S.A.) are added dropwise at room temperature, whilst stirring. The reaction is exothermic. The reaction mixture is then heated at the reflux temperature for 1 hour. The solution is filtered and concentrated completely under reduced pressure. The residual resin is dried for 1 hour in vacuo at 100° C and 0.1 mm Hg. This gives a yellowish, transparent resin which is readily soluble in hexane and mineral oil. (Additive No. 1).

EXAMPLE 2

12.4 g (0.1 mol) of 3-hydroxy-3-oxo-1,3-thiaphosphetane are suspended in 100 ml of toluene and 19.1 g (0.1 mol) of Primene 81-R (mixture of primary $C_{12}$–$C_{15}$ t-alkylamines, Rohm and Haas, U.S.A.) are added dropwise at room temperature, whilst stirring. Working up is carried out as in Example 1. (Additive No. 2).

If, in Example 2, the Primene 81-R is replaced by the amines listed in Table 1, an otherwise identical procedure gives the corresponding ammonium salts.

Table 1

| Additive No. | Amine | Melting point | Ammonium salt |
|---|---|---|---|
| 3 | n-dodecylamine | 93° C | (thiaphosphetane)·$H_2NC_{12}H_{25}$-n |
| 4 | n-octylamine | 78° C | (thiaphosphetane)·$H_2NC_8H_{17}$-n |
| 5 | Primene J.M.T. | resin | (thiaphosphetane)·$H_2NC_{18}H_{37}$-tert. |
| 6 | n-dibutylamine | 99° C | (thiaphosphetane)·$HN(C_4H_9$-n$)_2$ |
| 7 | n-tributylamine | resin | (thiaphosphetane)·$N(C_4H_9$-n$)_3$ |
| 8 | N,N-diethylaniline | resin | (thiaphosphetane)·$(C_2H_5)_2N$–$C_6H_5$ |
| 9 | N-methylaniline | resin | (thiaphosphetane)·$CH_3$-HN–$C_6H_5$ |
| 10 | 2,6-diethylaniline | 94–97° C | (thiaphosphetane)·2,6-$(C_2H_5)_2C_6H_3NH_2$ |

Table 1-continued

| Additive No. | Amine | Melting point | Ammonium salt |
|---|---|---|---|
| 11 | N-dimethyl-coroamine | 40–45° C | thiaphosphetane ring with $(CH_3)_2NC_{12-14}H_{25-29}$ |
| 12 | 70% of Primene JMT + 30% of hydroxy-ethylbutylamine | oil | thiaphosphetane ring with $H_2NC_{18}H_{37}$(tert.) 70%  and $C_4H_9NHCH_2CH_2OH$ 30% |
| 13 | di-tridecylamine | oil | thiaphosphetane ring with $HN(C_{13}H_{27})_2$ |
| 14 | tert.-octylamine | 174° C | thiaphosphetane ring with $H_2N-C(CH_3)_2-CH_2-C(CH_3)_3$ |

EXAMPLE 3

Stage 1

57 g (0.4 mol) of 3-chloro-3-oxo-1,3-thiaphosphetane and 25.5 g (0.115 mol) of phosphorus pentasulphide are heated to 100° C for 5 hours, whilst passing nitrogen through the mixture. The reaction mixture is then distilled under reduced pressure. The 3-chloro-3-thiono-1,3-thiaphosphetane which is thus obtained boils at 57° C/0.02 mm.

Stage 2

4.8 g (0.21 mol) of sodium are dissolved in 80 ml of methanol and the solution is saturated with hydrogen sulphide. The solution is heated to the boil whilst nitrogen is passed through and, whilst stirring vigorously at the same time, 15.8 g (0.1 mol) of 3-chloro-3-thiono-1,3-thiaphosphetane are added dropwise. Heating is then continued for 90 minutes and the mixture is cooled to room temperature and acidified with hydrochloric acid. The reaction mixture is concentrated completely under reduced pressure and the residue is suspended in hot toluene. After filtering off the sodium chloride which has precipitated, the solvent is completely stripped off reduced pressure and the residual greenish oil is ground with a little toluene. This gives 3-mercapto-3-thiono-1,3-thiaphosphetane with a melting point of 59° C.

Stage 3

4 g (0.028 mol) of 3-mercapto-3-thiono-1,3-thiaphosphetane in 100 ml of toluene are initially introduced and 5.6 g (0.0294 mol) of Primene 81-R are added, whilst stirring. The mixture is then concentrated completely under reduced pressure. This gives the Primene 81-R salt of 3-mercapto-3-thiono-1,3-thiaphosphetane in the form of a yellowish oil. (Additive No. 15).

EXAMPLE 4

The exceptional load-bearing properties of the additives, according to the invention, for lubricants are also shown in the test in the FZG gear wheel distortion test rig.

For this purpose, mixtures of the additive according to the invention in a non-doped mineral lubricating oil (viscosity: 20 cSt/50° C) were prepared and tested using the FZG machine according to DIN 51,354 (standard test A/8.3/90). For comparison, the non-doped mineral lubricating oil without an additive, and also mixtures of this lubricating oil with commercially available high-pressure additives, were also tested using the FZG machine.

The results of these tests are summarised in the Table which follows.

| Additive No. | Test No. | Concentration % by weight | ms [mg/KWh] | Power stage at which damage occurs |
|---|---|---|---|---|
|  | 1 | — | 0.61 | 7 |
| 1 | 2 | 0.03 | 0.1 | 12 |
| 2 | 3 | 0.05 | 0.1 | >12 |
| 2 | 4 | 0.08 | 0.1 | >12 |
| ZDTP*) | 5 | 0.5 | 0.29 | 11 |
| tri-phenyl phosphate | 6 | 1.0 | 0.37 | 10 |
| 5 | 7 | 0.1 |  | >12 |

*commercially available zinc dialkyldithiophosphate (about 80% active substance).

The distinct superiority of the additives, according to the invention, for lubricants over commercially available high-pressure additives can be seen at a markedly lower use concentration from the considerable reduction in the specific weight change of the gear wheels and also from a simultaneous improvement in the load-bearing capacity by 1–2 power stages.

EXAMPLE 5

The following values were determined using the four ball apparatus: (Tentative method IP 239/69, extreme pressure and wear lubricant test for oils and greases, four ball machine).

(1) I.S.L. = Initial Seizure Load: that is the load at which the oil film collapses within a load period of 10 seconds.

(2) W.L. = Weld Load. That is the load at which the 4 balls weld together within 10 seconds.

(3) W.S.D. = Wear Scar Diameter in mm: that is the average wear diameter when a load of 70 kg or 40 kg is applied for 1 hour.

Catenex 41 (tradename of Messrs. Shell) was used as the base oil.

| Additive No. | Concentration in % by weight | ISL (kg) | WL (kg) | WSD 70 kg and 40 kg |
|---|---|---|---|---|
| none | — | 60 | 160 | 2.42 (70 kg) |
|  |  |  |  | 1.10 (40 kg) |
| 1 | 1% | 145 | 415 | 0.78 (70 kg) |
| 2 | 1% | 130 | 420 | 0.77 (70 kg) |
| 3 | 1% |  | >200 | 0.8  (70 kg) |
| 5 | 1% | 200 | 295 | 0.78 (70 kg) |
| 11 | 1% |  | >200 | 0.7  (40 kg) |
| 12 | 1% |  | >200 | 0.9  (40 kg) |
| 13 | 1% | 100 | 230 | 0.75 (70 kg) |
| 15 | 1% | 100 | 280 | 0.99 (70 kg) |

What is claimed is:

1. A compound of the general formula I

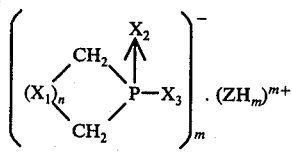

in which $X_1$, $X_2$ and $X_3$ independently of one another denote O or S and, if $X_1$ is O, $n$ denotes 1 and, if $X_1$ is S, $n$ denotes 1–6, and Z is a mono-acidic nitrogen-containing, oil-soluble organic base and $m$ denotes 1.

2. A compound to claim 1, of the formula I, in which $X_1$ is S and $n$ denotes 1–6 and $X_2$ and $X_3$ are O and $m$ and Z have the meaning defined in claim 1.

3. A compound according to claim 1, of the formula I, in which $X_1$ is S and $n$ is 1 and $X_2$ and $X_3$ denote O and $m$ and Z have the meaning defined in claim 1.

4. A compound according to claim 1 wherein Z is a primary, secondary or tertiary amine of the formula $(R_1)R_2NR_3$, in which $R_1$ and $R_2$ independently of one another denote hydrogen or an aliphatic or aromatic radical and $R_3$ denotes an aliphatic or aromatic radical.

5. A compound according to claim 4, wherein $R_1$ and $R_2$ independently of one another denote hydrogen or an aliphatic radical and $R_3$ denotes a phenyl group which is optionally substituted by alkyl groups.

6. A compound according to claim 4, wherein Z is a primary amine of the formula $H_2NR_3$, in which $R_3$ denotes an aliphatic radical.

7. A compound according to claim 6, wherein $R_3$ denotes branched or straight-chain alkyl or alkenyl, each with 6 to 40 C atoms, which are optionally interrupted by —O— or —S—.

8. A compound according to claim 7, wherein $R_3$ denotes branched or straight-chain alkyl or alkenyl, each with 8 to 24 C atoms.

9. A compound according to claim 1, of the formula I, in which $X_1$ is S and $n$ is 1–6 and $X_2$ and $X_3$ denote O and Z is a primary, secondary or tertiary amine of the formula $(R_1)R_2NR_3$, in which $R_1$ and $R_2$ independently of one another denote hydrogen or an aliphatic or aromatic radical and $R_3$ denotes an aliphatic or aromatic radical.

10. A compound according to claim 1, of the formula I, in which $X_1$ is S and $n$ is 1–6 and $X_2$ and $X_3$ denote O and Z is a primary amine of the formula $H_2NR_3$, in which $R_3$ denotes an aliphatic radical, and $m$ is 1.

11. A compound according to claim 10, wherein $n$ is 1 and the other symbols have the same meaning as in claim 10.

12. A compound according to claim 10, wherein $R_3$ denotes alkyl with 8 to 24 C atoms.

13. A compound according to claim 12, wherein $R_3$ denotes alkyl with 8 to 24 C atoms.

14. Compositions of matter consisting of a mineral and/or synthetic lubricating oil and from 0.001 to 5% by weight of a compound of the formula I according to claim 1.

15. A method for imparting high-pressure lubricating properties to lubricating oil which comprises adding from 0.001 to 5% by weight of a compound of the formula I according to claim 1.

* * * * *